(12) United States Patent
Jimenez

(10) Patent No.: US 8,628,577 B1
(45) Date of Patent: Jan. 14, 2014

(54) STABLE DEVICE FOR INTERVERTEBRAL DISTRACTION AND FUSION

(75) Inventor: Omar F. Jimenez, Gering, NE (US)

(73) Assignee: Ex Technology, LLC, Gering, NE (US)

(*) Notice: Subject to any disclaimer, the term of this patent is extended or adjusted under 35 U.S.C. 154(b) by 295 days.

(21) Appl. No.: 12/407,608

(22) Filed: Mar. 19, 2009

(51) Int. Cl.
*A61F 2/44* (2006.01)

(52) U.S. Cl.
USPC ................... 623/17.15; 623/17.16

(58) Field of Classification Search
USPC ............... 623/17.11–17.18; 606/249–279
See application file for complete search history.

(56) References Cited

U.S. PATENT DOCUMENTS

| | | |
|---|---|---|
| 2,106,088 A | 1/1938 | De Tar |
| 2,231,221 A | 2/1941 | Rector |
| 2,453,656 A | 11/1948 | Bullard |
| 2,666,334 A | 1/1954 | Nalle |
| 2,711,105 A | 6/1955 | Williams |
| 2,842,976 A | 7/1958 | Young |
| 3,386,128 A | 6/1968 | Vyvyan |
| 3,449,971 A | 6/1969 | Posh |
| 3,596,863 A | 8/1971 | Kaspareck |
| 3,708,925 A | 1/1973 | Ainoura |
| 3,709,132 A | 1/1973 | Farrell |
| 3,916,596 A | 11/1975 | Hawley |
| 4,261,211 A | 4/1981 | Haberland |
| 4,478,109 A | 10/1984 | Benjamin |
| 4,528,864 A | 7/1985 | Craig |
| 4,559,717 A | 12/1985 | Scire |
| 4,630,495 A | 12/1986 | Smith |
| 4,691,586 A | 9/1987 | Van Leijenhorst |
| 4,694,703 A | 9/1987 | Routson |
| 4,869,552 A | 9/1989 | Tolleson |
| 5,133,108 A | 7/1992 | Esnault |
| 5,181,371 A | 1/1993 | Deworth |
| 5,196,857 A | 3/1993 | Chiappetta |

(Continued)

FOREIGN PATENT DOCUMENTS

| | | |
|---|---|---|
| EP | 1342456 | 9/2003 |
| EP | 1552797 A2 | 7/2005 |

(Continued)

OTHER PUBLICATIONS

International Search Report and Written Opinion of the International Searching Authority or the Declaration dated Sep. 27, 2010, International Application No. PCT/US2009/069876, filed Dec. 30, 2009, 12 pages.

(Continued)

*Primary Examiner* — David Isabella
*Assistant Examiner* — Randy Shay
(74) *Attorney, Agent, or Firm* — Patterson Thuente Pedersen, P.A.

(57) ABSTRACT

Improved methods and apparatuses for vertebral body distraction and fusion in accordance with various embodiments employ mechanisms for stabilizing a device so that the device can stay in the body and stably support the disc space during vertebral fusion following distraction of the adjacent vertebra by operation of the device. The device is inserted into the disc space and distracted from a compressed configuration to an expanded configuration to distract the disc space. Mechanisms for stabilizing the device in the expanded configuration constrain the device to zero degrees of freedom of movement to allow the device to stably support the disc space. A bone growth stimulant for promoting vertebral fusion can be inserted into an open space defined by the device, which continues to stably support the disc space during vertebral fusion.

13 Claims, 18 Drawing Sheets

(56) References Cited

U.S. PATENT DOCUMENTS

| | | | |
|---|---|---|---|
| 5,198,932 A | | 3/1993 | Takamura |
| 5,222,986 A | * | 6/1993 | Wright ............................ 623/64 |
| 5,374,556 A | | 12/1994 | Bennett |
| 5,439,377 A | | 8/1995 | Milanovich |
| 5,664,457 A | | 9/1997 | Nejati |
| 5,904,479 A | | 5/1999 | Staples |
| 5,960,670 A | | 10/1999 | Iverson |
| 5,980,252 A | | 11/1999 | Samchukov |
| 5,988,006 A | | 11/1999 | Fleytman |
| 6,045,579 A | * | 4/2000 | Hochshuler et al. ....... 623/17.16 |
| 6,056,491 A | | 5/2000 | Hsu |
| 6,350,317 B1 | | 2/2002 | Hao et al. |
| 6,378,172 B1 | | 4/2002 | Schrage |
| 6,454,806 B1 | | 9/2002 | Cohen |
| 6,484,608 B1 | | 11/2002 | Ziavras |
| 6,517,772 B1 | | 2/2003 | Woolf |
| 6,641,614 B1 | * | 11/2003 | Wagner et al. ............. 623/17.15 |
| 6,719,796 B2 | | 4/2004 | Cohen |
| 6,772,479 B2 | | 8/2004 | Hinkley |
| 6,802,229 B1 | | 10/2004 | Lambert |
| 6,808,537 B2 | | 10/2004 | Michelson |
| 6,863,673 B2 | | 3/2005 | Gerbec |
| 6,953,477 B2 | | 10/2005 | Berry |
| 7,018,415 B1 | | 3/2006 | McKay |
| 7,051,610 B2 | | 5/2006 | Stoianovici |
| 7,070,598 B2 | * | 7/2006 | Lim et al. ........................ 606/99 |
| 7,201,751 B2 | | 4/2007 | Zucherman |
| 7,273,373 B2 | | 9/2007 | Horiuchi |
| 7,308,747 B2 | | 12/2007 | Smith |
| 7,316,381 B2 | | 1/2008 | Hacker |
| 7,410,201 B1 | | 8/2008 | Wilson |
| 7,425,103 B2 | | 9/2008 | Perez-Sanchez |
| 7,435,032 B1 | | 10/2008 | Murphey |
| 7,584,682 B2 | | 9/2009 | Hsiao |
| 7,708,779 B2 | | 5/2010 | Edie |
| 7,753,958 B2 | | 7/2010 | Gordon |
| 7,758,648 B2 | | 7/2010 | Castleman |
| 2003/0077110 A1 | | 4/2003 | Knowles |
| 2003/0233145 A1 | | 12/2003 | Landry |
| 2004/0225364 A1 | | 11/2004 | Richelsoph et al. |
| 2005/0000228 A1 | | 1/2005 | De Sousa |
| 2005/0033431 A1 | | 2/2005 | Gordon |
| 2005/0095384 A1 | | 5/2005 | Wittmeyer |
| 2005/0113924 A1 | | 5/2005 | Buttermann |
| 2005/0175406 A1 | | 8/2005 | Perez-Sanchez |
| 2006/0004447 A1 | | 1/2006 | Mastrorio |
| 2006/0004455 A1 | | 1/2006 | Leonard et al. |
| 2006/0025862 A1 | | 2/2006 | Villiers et al. |
| 2006/0129244 A1 | | 6/2006 | Ensign |
| 2006/0149385 A1 | | 7/2006 | McKay |
| 2007/0032791 A1 | | 2/2007 | Greenhalgh |
| 2007/0049943 A1 | | 3/2007 | Moskowitz |
| 2007/0129730 A1 | | 6/2007 | Woods et al. |
| 2007/0185577 A1 | | 8/2007 | Malek |
| 2007/0191954 A1 | * | 8/2007 | Hansell et al. ............. 623/17.15 |
| 2007/0191958 A1 | | 8/2007 | Abdou |
| 2007/0222100 A1 | | 9/2007 | Husted et al. |
| 2007/0282449 A1 | | 12/2007 | Villiers |
| 2007/0293329 A1 | | 12/2007 | Glimpel |
| 2007/0293948 A1 | * | 12/2007 | Bagga et al. ............... 623/17.11 |
| 2008/0026903 A1 | | 1/2008 | Flugrad |
| 2008/0100179 A1 | | 5/2008 | Ruggeri |
| 2008/0168855 A1 | | 7/2008 | Giefer |
| 2008/0188941 A1 | | 8/2008 | Grotz |
| 2008/0210039 A1 | | 9/2008 | Brun |
| 2008/0221694 A1 | | 9/2008 | Warnick |
| 2009/0012564 A1 | | 1/2009 | Chirico |
| 2009/0164017 A1 | | 6/2009 | Sommerich |
| 2010/0094305 A1 | | 4/2010 | Chang |
| 2010/0185291 A1 | | 7/2010 | Jimenez et al. |
| 2010/0209184 A1 | | 8/2010 | Jimenez et al. |

FOREIGN PATENT DOCUMENTS

| | | |
|---|---|---|
| EP | 1881209 | 10/2008 |
| JP | 05-81194 | 11/1993 |
| JP | 2004-301135 | 10/2004 |
| JP | 2008-208932 | 9/2008 |
| WO | WO 2004/026188 | 4/2004 |
| WO | WO2004/109155 | 12/2004 |
| WO | WO 2005/081330 | 9/2005 |
| WO | WO 2005/096975 A2 | 10/2005 |
| WO | WO 2006/094535 | 9/2006 |
| WO | WO 2006/116052 | 11/2006 |
| WO | WO 2006/125329 | 11/2006 |
| WO | WO 2007/002583 | 1/2007 |
| WO | WO 2007/009107 A2 | 1/2007 |
| WO | WO 2007/028140 | 3/2007 |
| WO | WO 2007/076377 A2 | 7/2007 |
| WO | 2007/111979 * | 10/2007 |
| WO | WO 2008/137192 | 11/2008 |
| WO | WO 2009/018349 | 2/2009 |
| WO | WO 2010/078520 | 12/2009 |

OTHER PUBLICATIONS

International Search Report and Written Opinion of the International Searching Authority or the Declaration dated Nov. 29, 2010, International Application No. PCT/US2009/069958, filed Dec. 31, 2009, 9 pages.

Wenzel Spine, Inc., *VariLift®-L Expandable Interbody Fusion Device: A proven solution for stand-alone fusion*, Product Overview, 12 pages, © 2010.

Peter A. Halverson, et. al., Tension-based Multi-stable Compliant: Rolling-contact Elements, Department of Mechanical Engineering, Brigham Young University, Provo UT, USA 84602 (34 pages), 2007.

Just L. Herder, Force Directed Design of Laparoscopic Forceps, 1998, ASME Design Engineering Technical Conference (8 pages).

Alexander H. Slocum, Fundamentals of Design (2005).

Amelie Jeanneau, et. al., A Compliant Rolling Contact Joint and its Application in a 3-DOF Planar Parallel Mechanism with Kinematic Analysis, ASME (2004) Design Engineering Technical Conferences (9 pages).

Application and File History of U.S. Appl. No. 12/651,266, Inventors Jimenez et al., filed Dec. 31, 2009.

Application and File History of U.S. Appl. No. 12/650,994, Inventors Jimenez et al., filed Dec. 31, 2009.

Application and File History of U.S. Appl. No. 12/841,465, Inventors Jimenez et al., filed Jul. 22, 2010.

Application and File History of U.S. Appl. No. 12/841,869, Inventors Jimenez et al., filed Jul. 22, 2010.

W. Kiisswetter, *A Supplementary Instrumentation for Posterior Fusion of Spine in Scoliosis*, Archives of Orthopedic Traumatic Surgery, 1980, 1 page.

Chou et al., *Efficacy of Anterior Cervical Fusion: Comparison of Titanium Cages, polyetheretherketone (PEEK) cages and autogenous bone grafts*, Journal of Clinical Neuroscience, 2008, pp. 1240-1245.

Hunter et al., *Overview of Medical Devices*, Department of Radiology, University of Arizona, Aug. 2001, pp. 89-140, vol. 30, No. 4, ISSN: 0363-0188.

Notification of Transmittal of the International Search Report and the Written Opinion of the International Searching Authority or the Declaration, Application No. PCT/US2010/042941, mailed Apr. 25, 2011.

International Search Report, Application No. PCT/US2010/042915, mailed Apr. 22, 2011.

European Application No. EP 09837185, European Search Report dated May 14, 2013, 7 pages.

* cited by examiner

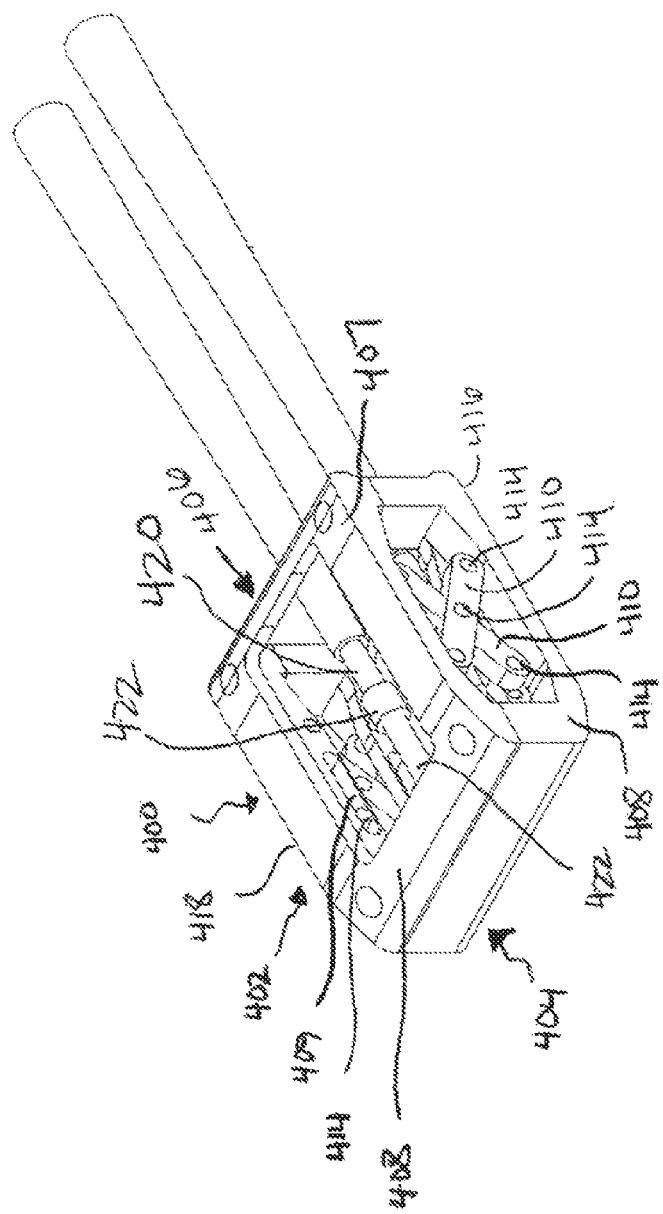

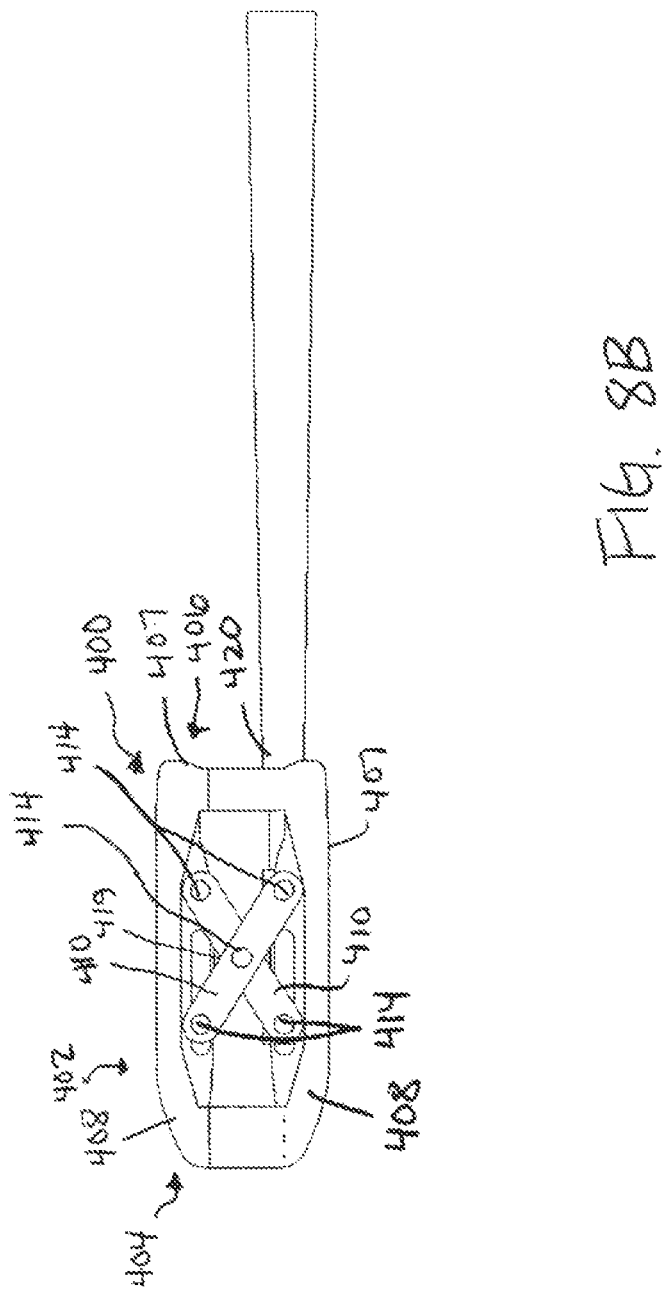

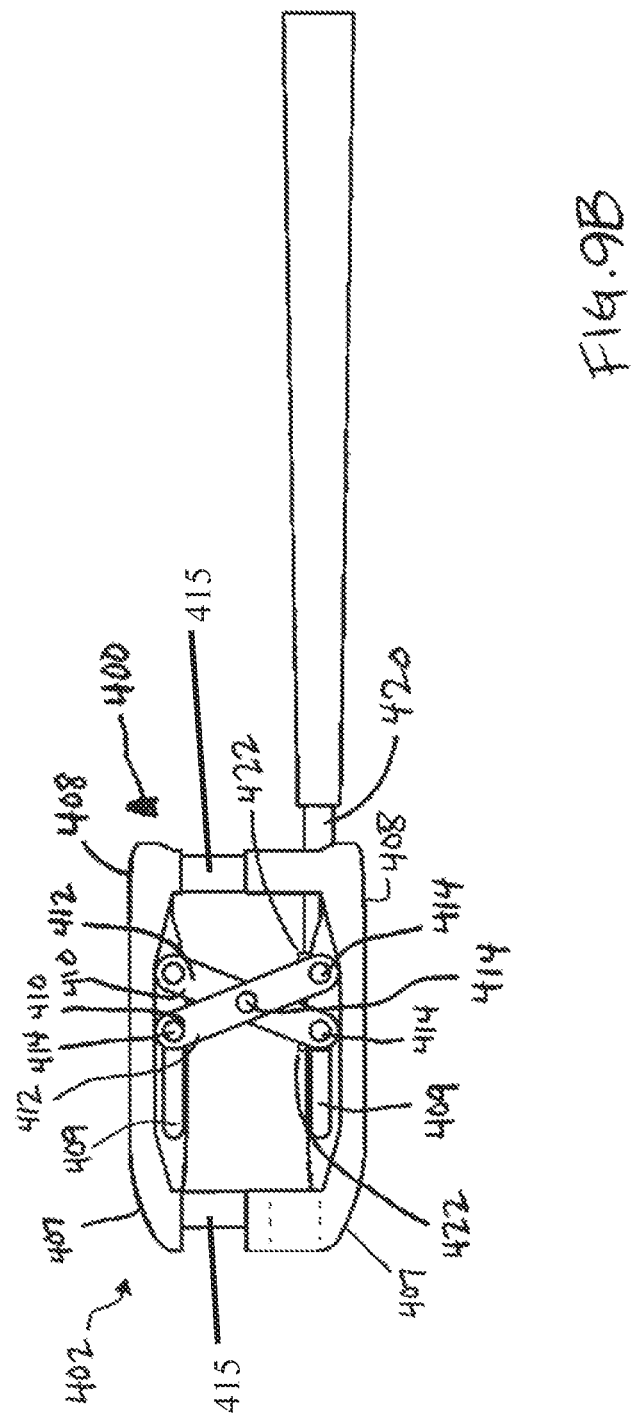

STABLE DEVICE FOR INTERVERTEBRAL DISTRACTION AND FUSION

PRIORITY APPLICATIONS

This application is related to U.S. Provisional Application No. 61/038,039, filed Mar. 19, 2008, and U.S. application Ser. No. 12/118,767, filed May 12, 2008, each of which is hereby fully incorporated herein by reference.

FIELD OF THE INVENTION

The present invention relates to the distraction and fusion of vertebral bodies. More specifically, the present invention relates to devices and associated methods for distraction and fusion of vertebral bodies that remain stable when implanted and facilitate fusion following their use for distraction. In addition, the present invention aids in the correction of spinal deformity by reducing a collapse disc and establishing sagittal allingment, lordosis or kyphosis.

BACKGROUND OF THE INVENTION

The concept of intervertebral fusion for the cervical and lumbar spine following a discectomy was generally introduced in the 1960s. It involved coring out a bone graft from the hip and implanting the graft into the disc space. The disc space was prepared by coring out the space to match the implant. The advantages of this concept were that it provided a large surface area of bone to bone contact and placed the graft under loading forces that allowed osteoconduction and induction enhancing bone fusion. However, the technique is seldom practiced today due to numerous disadvantages including lengthy operation time, destruction of a large portion of the disc space, high risk of nerve injury, and hip pain after harvesting the bone graft.

Presently, at least two devices are commonly used to perform the intervertebral portion of an intervertebral body fusion: the first is the distraction device and the second is the intervertebral body fusion device, often referred to as a cage. Cages can be implanted as standalone devices or as part of a circumferential fusion approach with pedicle screws and rods. The concept is to introduce an implant that will distract a collapsed disc and decompress the nerve root, allow load sharing to enhance bone formation and to implant a device that is small enough to allow implantation with minimal retraction and pulling on nerves.

In a typical intervertebral body fusion procedure, a portion of the intervertebral disc is first removed from between the vertebral bodies. This can be done through either a direct open approach or a minimally invasive approach. Disc shavers, pituitary rongeours, curettes, and/or disc scrapers can be used to remove the nucleus and a portion of either the anterior or posterior annulus to allow implantation and access to the inner disc space. The distraction device is inserted into the cleared space to enlarge the disc space and the vertebral bodies are separated by actuating the distraction device. Enlarging the disc space is important because it also opens the foramen where the nerve root exists. It is important that during the distraction process one does not over-distract the facet joints. An intervertebral fusion device is next inserted into the distracted space and bone growth factor, such as autograft, a collagen sponge with bone morphogenetic protein, or other bone enhancing substance may be inserted into the space within the intervertebral fusion device to promote the fusion of the vertebral bodies.

Intervertebral fusion and distraction can be performed through anterior, posterior, oblique, and lateral approaches. Each approach has its own anatomic challenges, but the general concept is to fuse adjacent vertebra in the cervical thoracic or lumbar spine. Devices have been made from various materials. Such materials include cadaveric cancellous bone, carbon fiber, titanium and polyetheretherketone (PEEK). Devices have also been made into different shapes such as a bean shape, football shape, banana shape, wedge shape and a threaded cylindrical cage.

U.S. Pat. Nos. 7,070,598 and 7,087,055 to Lim et al. disclose minimally invasive devices for distracting the disc space. The devices include scissor-jack-like linkages that are used to distract a pair of endplates associated with adjacent vertebra from a first collapsed orientation to a second expanded orientation. A pull arm device is used to deliver and distract the device in the disc space. However, the device is primarily used for distraction and not subsequent vertebral fusion. The device would not work as a fusion device, because once the pull arm is disconnected from the device, the device will not be stable enough to maintain proper spacing of the vertebrae until fusion can occur. The endplates of the device are also solid and do not permit bone growth for successful fusion.

U.S. Patent Publication No. 2008/0114367 to Meyer discloses a device that uses a scissor-jack-like arrangement to distract a disc space. To solve the instability problem of the scissor-jack arrangement, a curable polymer is injected to fill the disc space and the distraction device is disabled from attempting to support the load. The curable polymer and disabling of the device are necessary because the device could not adequately support the distracted disc space. The base plates of the device have at least two or more degrees of freedom, collectively, in a distracted position and are therefore not stable under the loads encountered supporting the disc space. Absent injection of the polymer, and the support and control supplied by the implanting physician via the removable distraction tool, the base plates would collapse, which could cause severe damage to the vertebral bodies.

Accordingly, there is a need in the art for a device that can distract adjacent vertebral bodies in a minimally invasive manner while providing stable support for the disc space during fusion.

SUMMARY OF THE INVENTION

Improved methods and apparatuses for vertebral body distraction and fusion in accordance with various embodiments of the present invention employ a means for stabilizing a device so that it can stay in the body and stably support the disc space during vertebral fusion following its use as a distraction device. The device is expected to be capable of supporting prolonged, compressive loading of greater than 2000-3000 [N]; oblique shear loading of greater than 1200-1500 [N]; and torsion of greater than 10-20 [N]. The device is inserted into the disc space and distracted from a compressed configuration to an expanded configuration to distract the disc space. Mechanisms for stabilizing constrains of the device to zero, or fewer, degrees of freedom of movement enables the device to stably support the disc space. A bone growth stimulant for promoting vertebral fusion can be inserted into an open space defined by the device, which continues to stably support the disc space during vertebral fusion.

In one embodiment, a device can be used for both intervertebral distraction and fusion of an intervertebral disc space. The device can include a top base plate having a top bearing surface configured to interface with an end plate of a superior vertebra of the intervertebral disc space and a bottom base plate having a bottom bearing surface configured to interface with an end plate of an inferior vertebra of the intervertebral disc space. A first arm and a second arm can each be hinged and connected to the top base plate and the bottom base plate. A threaded member can extend through the first arm and into the second arm and be configured such that rotation of the threaded member in a first direction causes expansion of the first and second arms such that the top bearing surface and bottom bearing surface move away from each other into a distracted position. The device also includes a means for stabilizing the top base plate and bottom base plate such that the device has zero degrees of freedom of movement in the distracted position and is designed to remain in the body and stably maintain the intervertebral disc space during vertebral fusion following being moved to the distracted position.

Optionally, some flexibility or compliance may be built into the device, while maintaining the stability of the device, by selecting flexible materials for some of the rigid members and or by manipulating the fits of the numerous joints. Flexible material may also be added to, in, around, or between elements of the device to additionally support flexibility, while maintaining, or in some embodiments, enhancing, the stability of the device by reducing potential hysteresis.

In another embodiment, a method of intervertebral body distraction and fusion involves implantation of a distractible intervertebral body fusion device into an intervertebral disc space. The device is inserted such that a top bearing surface of a top base plate of the device interfaces with an end plate of a superior vertebra of the disc space and a bottom bearing surface of a bottom base plate interfaces with an end plate of an inferior vertebra of the disc space. The device is distracted into an expanded configuration such that the top base plate and bottom base plate are vertically separated from each other to expand the disc space. A bone growth promoting material can then be inserted into the disc space into an open space defined by the device to encourage bone growth and fusion through one or more openings in the base plates. The bone growth promoting material can then be allowed to aid in intervertebral fusion of the adjacent vertebrae while the device stably supports the vertebrae with zero degrees of freedom of movement.

The above summary of the various embodiments of the invention is not intended to describe each illustrated embodiment or every implementation of the invention. This summary represents a simplified overview of certain aspects of the invention to facilitate a basic understanding of the invention and is not intended to identify key or critical elements of the invention or delineate the scope of the invention.

BRIEF DESCRIPTION OF THE DRAWINGS

The invention may be more completely understood in consideration of the following detailed description of various embodiments of the invention in connection with the accompanying drawings, in which:

FIG. 8A is a perspective view of a distractible intervertebral body fusion device according to an aspect of the present invention.

FIG. 8B is a side view of the distractible intervertebral body fusion device of FIG. 8A.

FIG. 9B is a side view of the distractible intervertebral body fusion device of FIG. 8A in an expanded configuration.

Figure 1A:
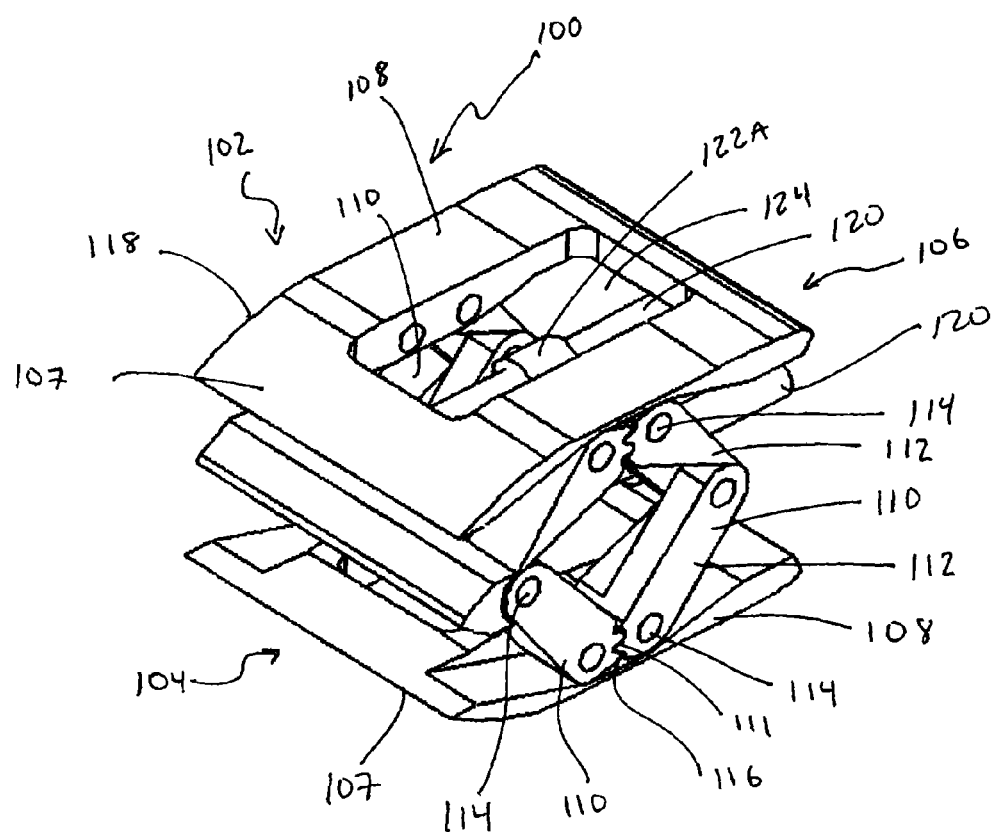
FIG. 1A is a perspective view of an embodiment of a distractible intervertebral body fusion device according to an aspect of the present invention.

While the invention is amenable to various modifications and alternative forms, specifics thereof have been shown by way of example in the drawings and will be described in detail. It should be understood, however, that the intention is not to limit the invention to the particular embodiments described. On the contrary, the intention is to cover all modifications, equivalents, and alternatives falling within the spirit and scope of the invention.

DETAILED DESCRIPTION OF THE DRAWINGS

In the following detailed description of the present invention, numerous specific details are set forth in order to provide a thorough understanding of the present invention. However, one skilled in the art will recognize that the present invention may be practiced without these specific details. In other instances, well-known methods, procedures, and components have not been described in detail so as to not unnecessarily obscure aspects of the present invention.

Figure 1B:
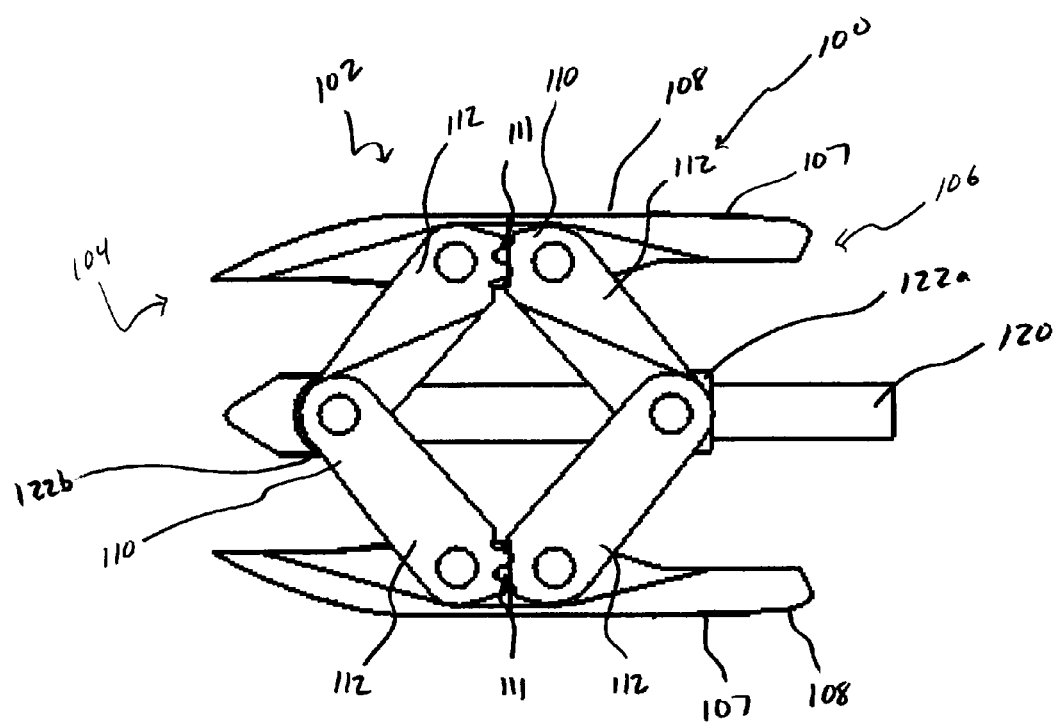
FIG. 1B is a side view of the distractible intervertebral body fusion device of FIG. 1A.
Figure 1C:
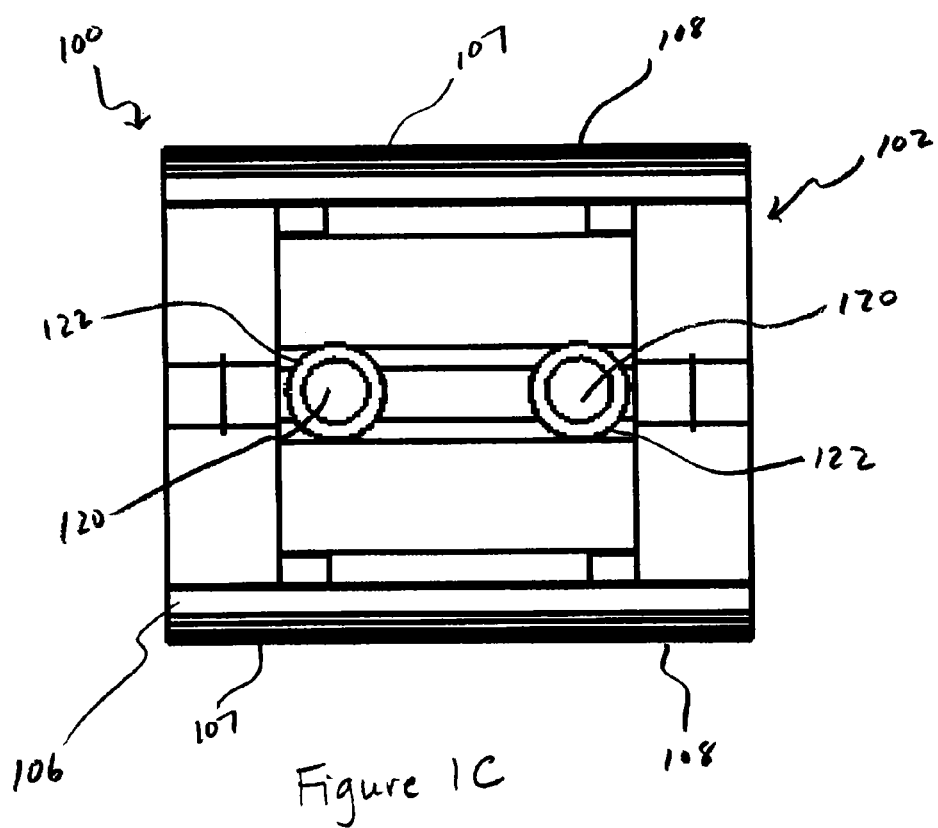
FIG. 1C is an end view of the distractible intervertebral body fusion device of FIG. 1A.
Figure 1D:
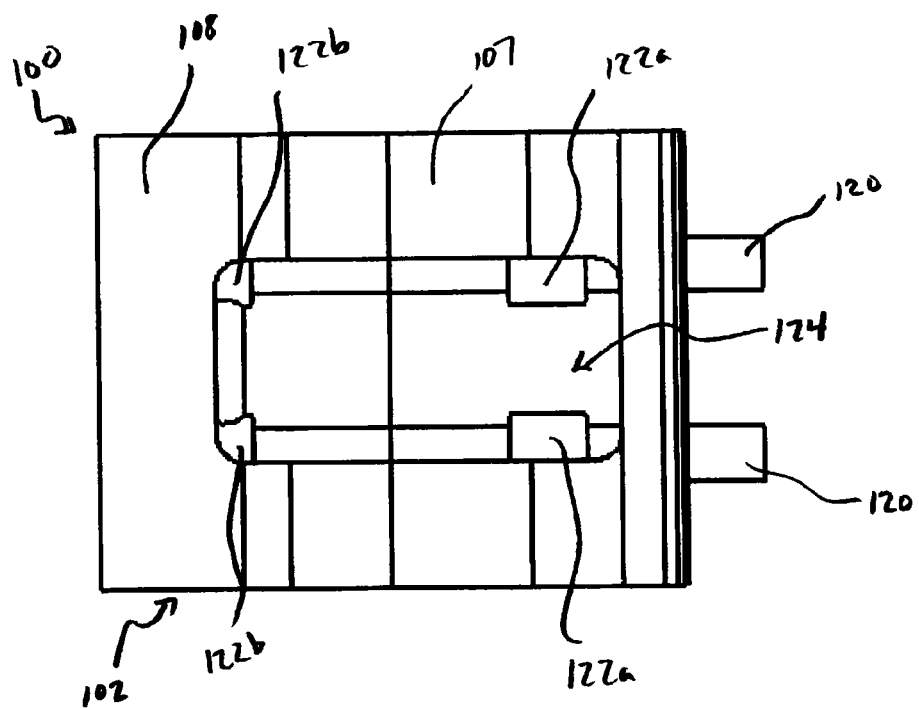
FIG. 1D is a top view of the distractible intervertebral body fusion device of FIG. 1A.

Referring to FIGS. 1A-1C, there can be seen a distractible intervertebral body fusion device 100 according to an aspect of the present invention. Device 100 includes a device body 102. Device body 102 can include a nose portion 104, a rear portion 106, a pair of opposed base plates 108 having outer bearing surfaces 107, and arms 110. As used throughout this disclosure, "bearing surface" refers to the outside surface of a base plate that interfaces with the endplate of a vertebra. Each arm 110 can include a pair of structural members 112 hingedly attached to each other, with each structural member 112 hingedly attached to one of the base plates 108. In one embodiment, structural members 112 are hinged to each other and to base plates 108 with pins 114. Structural members 112 on opposing arms 110 can interlock with each other via gear teeth 111 positioned on the ends of structural members 112. Gear teeth 111 are arranged so as to keep the device 100 stable when it is distracted within the body and supporting a load. In one embodiment, device 100 includes a pair of arms 110 on a first side 116 and a pair of arms 110 on a second side 118 of device 100.

Threaded members 120, such as screws, can be inserted through blocks 122a attached to the arm 110 nearest the rear portion 106 and into blocks 122b attached to the arm 110 nearest the nose portion 104. Actuation of threaded members 120 in a first direction drives blocks 122 closer together, which causes expansion of arms 110 and distraction of base plates 108. Actuation of threaded members 120 in the opposite direction would drive blocks 122 apart, thereby bringing base plates 108 closer together. This back-drivability of the device 100 is helpful for sizing the device 100 and removing the device 100 if necessary, such as in the event of postsurgical infection or trauma. Portions of the threaded members 120 may be reverse threaded to allow distraction without changing the position of the threaded members along the respective axes of the threaded members helping to keep the device from adversely interacting with the anatomy of the patient. In one embodiment, blocks 122a can be tapped to accommodate threaded members 120 and blocks 122b can provide a clearance fit with threaded members 120. When threaded members 120 are actuated, this allows blocks 122b to be pulled towards blocks 122a, causing the device 100 to distract. Alternatively, instead of threaded members 120 extending through a separate block portion 122 of arms 110 connected to structural members 112, threaded members 120 can extend through apertures directly through structural members 112.

Figure 13:
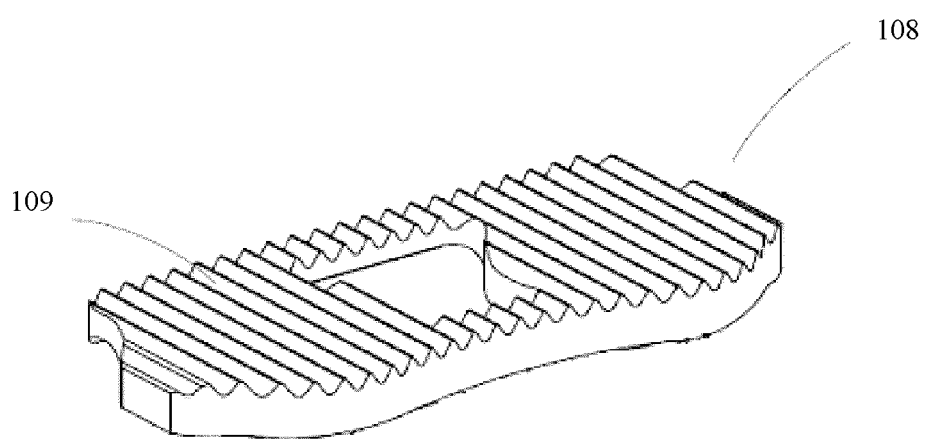
FIG. 13 is a perspective view of a base plate for a distractible intervertebral body fusion device according to an embodiment of the present invention.

In one embodiment, each base plate 108 includes an opening 124 to facilitate bone growth through the device 100. Openings 124 promote vertebral fusion because bone can grow directly through the device 100. Although depicted as being generally rectangular, opening 124 can comprise any shape. Alternatively, a generally solid surface or a surface with multiple openings can be provided on each base plate 108. Endplates 108 can also have a rough surface or teeth 109 (FIG. 13) to create friction with the base plates of the vertebra to prevent accidental extrusion of he device 100 or to promote bone growth for successful fusion. Nose portion 104 can be tapered to facilitate insertion of the device 100 into the disc space. Rear portion 106 can also be tapered.

In various embodiments, device body 102 is shaped to be ergonomic. Device body 102 can have various shapes, such as, for example, rectangular or kidney-shaped. A kidney-shaped device body 102 maximizes contact between the device and the vertebral bodies because the base plates of vertebrae tend to be slightly concave. One or both ends of the device may also be tapered to facilitate insertion. This minimizes the amount of force needed to initially separate the vertebral bodies. In addition, the device may be convex along both its length and its width, or bi-convex. Device body can also be comprised of various materials. Such materials can include, for example, titanium, steel, PEEK and carbon fiber. Device can also be constructed in various sizes depending on the type of vertebra and size of patient with which it is being used. In some embodiments, the threaded member 120 can be micro-machined, or split along its length and reconnected using a bellows or flexible torque transmission device, to be able to operate through an angle that may be necessitated by the shape of the device.

Figure 2A:
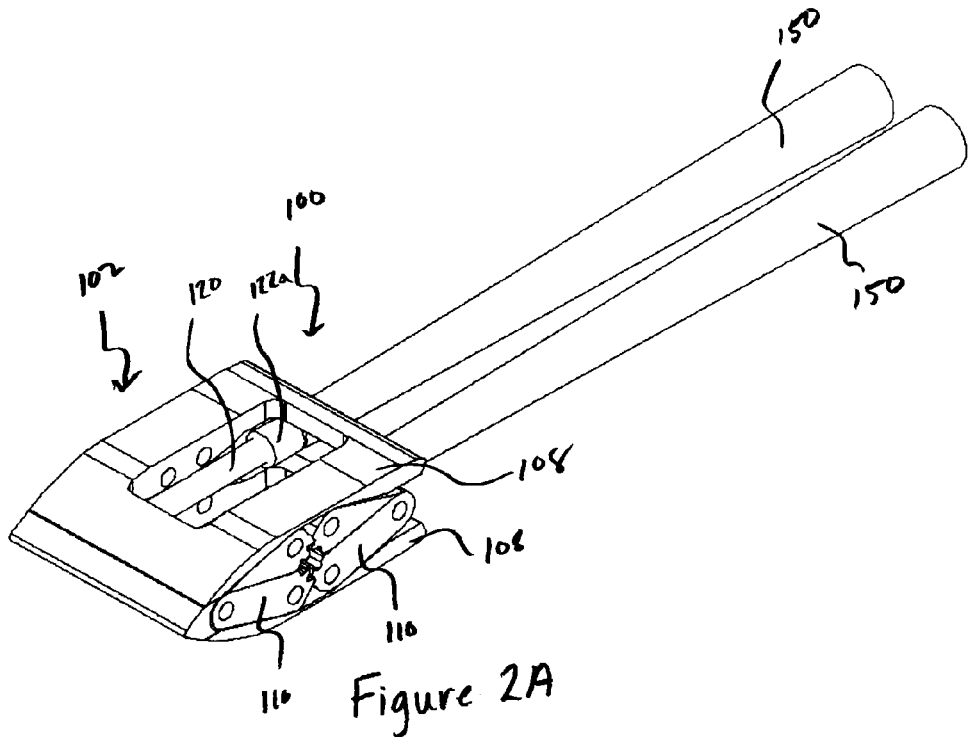
FIG. 2A is a perspective view of the distractible intervertebral body fusion device of FIG. 1A in a compressed configuration.
Figure 2B:
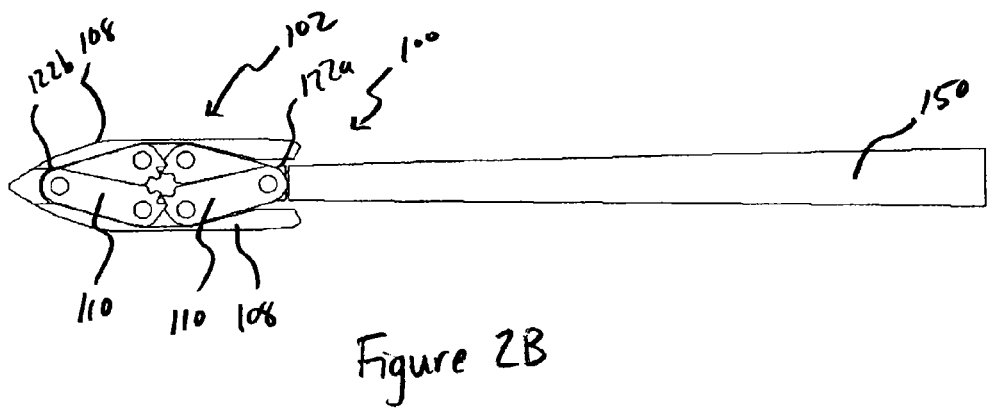
FIG. 2B is a side view of the distractible intervertebral body fusion device of FIG. 1A in a compressed configuration.
Figure 3A:
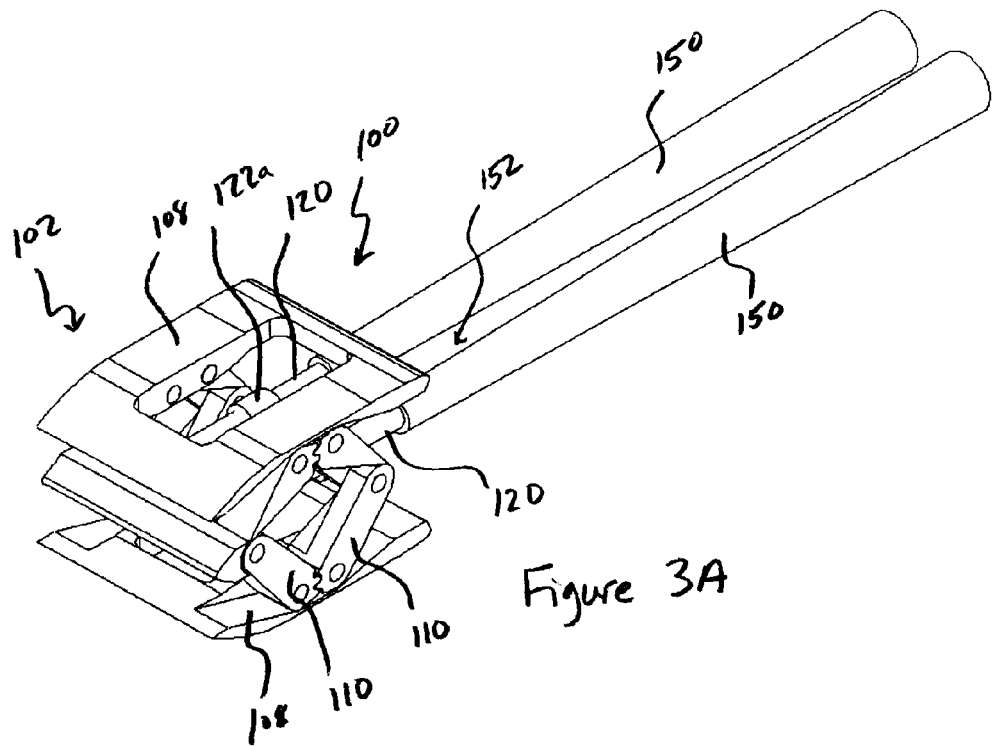
FIG. 3A is a perspective view of the distractible intervertebral body fusion device of FIG. 1A in an expanded configuration.
Figure 3B:
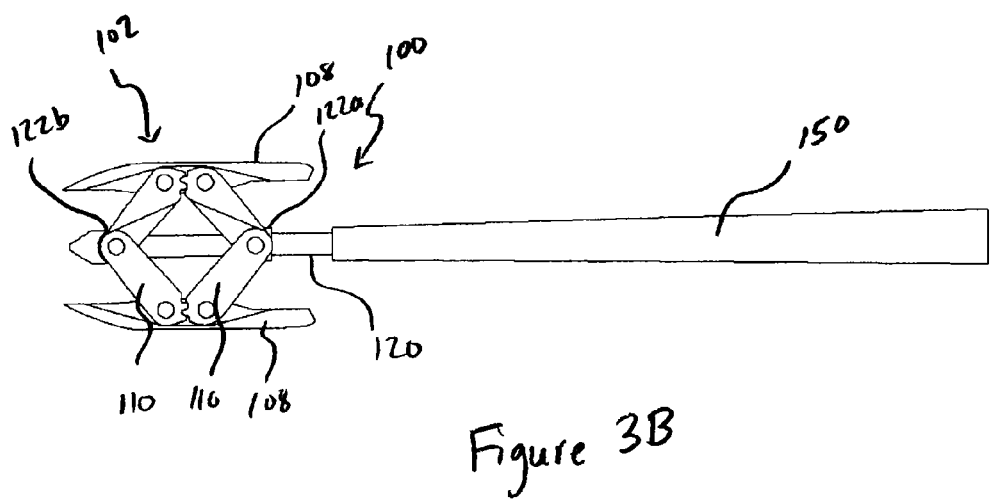
FIG. 3B is a side view of the distractible intervertebral body fusion device of FIG. 1A in an expanded configuration.

Device 100 can be placed between adjacent vertebrae or vertebral bodies and used to distract the endplates of the adjacent vertebral bodies and subsequently serve as a fusion device. One or more insertion tools 150 can be used to insert and distract device 100. Referring to FIGS. 2A and 2B, the device body 102 can be seen in its initial compressed configuration. In FIGS. 3A and 3B, device body 102 is in an expanded configuration. Insertion tools 150 can be connected to threaded members 120 and first used to insert device 100 into a desired location. Device 100 can be inserted with tapered nose portion 104 first. One device 100 can be inserted, or, for additional support, two devices 100 can be inserted. Two devices 100, each sized to be inserted within one-half of the evacuated disc space, can be especially useful for treating larger patients in which the device may encounter higher loads. In another embodiment, three or more small devices can be inserted into the disc space in order to very accurately control the orientation and distance between the discs. Three or more distraction mechanisms may be positioned circumferentially between two circular endplates to result in very accurate control and orientation of the base plates. Such a device would resemble a hexapod.

To distract device 100, insertion tools 150 can be used to rotate threaded members 120 in a first direction. This causes blocks 122b to be pulled towards blocks 122a, which causes arms 110 to expand and base plates 108 to distract. Threaded members 120 can be actuated the same amount (either simultaneously or independently) for uniform distraction or can be actuated different amounts for non-uniform distraction with one side 116 or 118 of the device higher than the other. The endplates 108 or other elements of the device 100 may in some embodiments be made compliant for exaggerated non-uniform distraction while maintaining the stability of the device 100. Once base plates 108 are distracted to a desired degree, insertion tools can be disconnected from threaded members 120 and the device 100 can remain within the body. In one embodiment, a locking mechanism can be utilized to prevent rotation of the threaded members to ensure the device remains in the distracted state. In one embodiment, the locking mechanism can be activated with the insertion device. In one embodiment, locking may be enhanced by tightening a threaded nut (not shown) against one or more of the threaded blocks 122.

Figure 12:
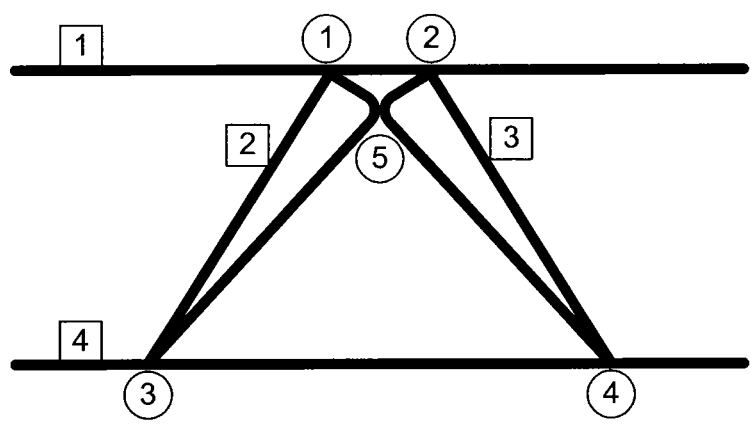
FIG. 12 is a simplified of a distractible intervertebral body fusion device according to an aspect of the present invention.

Device 100 is capable of stably supporting the vertebral bodies in the distracted position. Interlocked gear teeth 111 of structural members 112 in addition to threaded members 120 interlocked with blocks 122 constrain the device such that there are zero, or fewer, degrees of freedom. A typical four bar planar linkage has four links and has four kinematic pairs each limiting two degrees of freedom and each allowing one degree freedom resulting in the four bar planar linkage having one degree of freedom overall. Gears such as those of gear teeth 111 may be added as described above to create one additional kinematic pair limiting the device in one or more additional degree(s) of freedom thus resulting in an overall freedom of zero or fewer degrees of freedom. That is, none of the linkages that comprise the device are capable of independent movement with respect to the other linkages. According to Gruebler's equation the number of degrees of freedom of a planar linkage=3*(n−1)−2f, where n is the number of links in the linkage and f is the number of one degree of freedom kinematic pairs in the linkage. Referring to FIG. 12, a simplified view of a distractible intervertebral body fusion device can represent device 100, where the symbol (5) represents the gear teeth. Without the gear teeth, the device has four links and four kinematic pairs and therefore 3*(4−1)−2*4=1 degree of freedom. The device would therefore be unstable when supporting a load. Adding in the gear teeth, however, adds a kinematic coupling and there are therefore 3*(4−1)−2*5=−1 degrees of freedom. The device is therefore actually over constrained (meaning that there are additional constraints beyond the minimum necessary to make it stable), and stable under loading conditions. This allows device 100 to stably support the disc space upon distraction. In some embodiments, a crush surface or compliant materials may be used in concert with or in place of the interlocking gear teeth 111 or hinges 114 to minimize hysteresis that may be present in the device 100 and due to clearance in the gear teeth 111 and hinge mechanisms 114 necessary for overcoming the over-constraint in devices having fewer than zero degrees of freedom.

Once device is inserted and supporting the adjacent vertebral bodies, it can be utilized to promote vertebral fusion. Following distraction, a bone growth stimulant, such as autograft, bone morphogenic protein, or bone enhancing material, can be delivered into an open area defined within the device. In one embodiment, bone growth stimulant is delivered after insertion tools 150 are disconnected. In another embodiment, bone growth stimulant is delivered through an open area between insertion tools 150. In a further embodiment, bone growth stimulant can be delivered by the insertion tools 150 through a hollow chamber within insertion tools 150. Device is then capable of supporting in-vivo loads during the 6 to 12 weeks that fusion occurs between the vertebral bodies. In one embodiment, openings 124 in base plates 108 promote and allow for bone growth into and through the device 100.

Figure 4A:
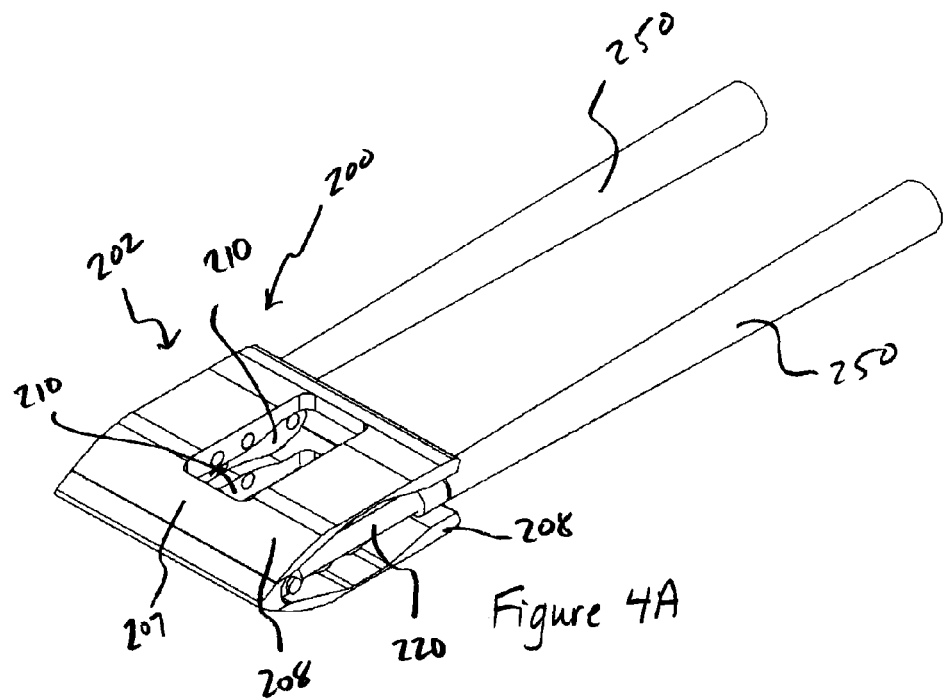
FIG. 4A is a perspective view of an embodiment of a distractible intervertebral body fusion device according to an aspect of the present invention.
Figure 4B:
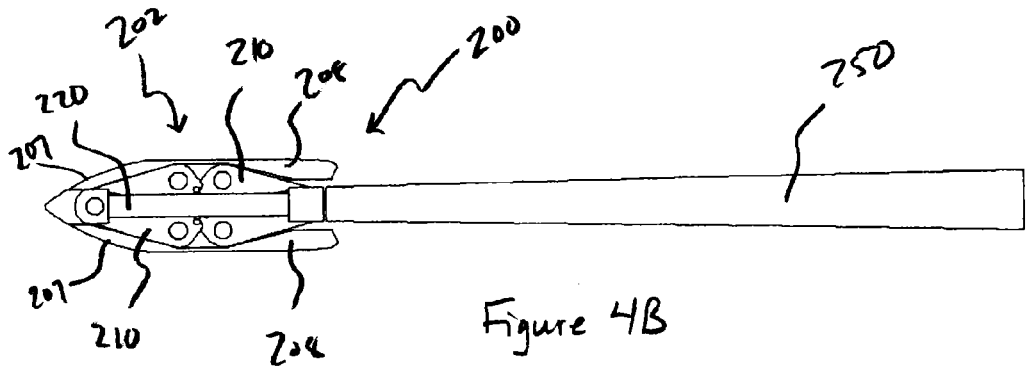
FIG. 4B is a side view of the distractible intervertebral body fusion device of FIG. 4A.
Figure 4C:
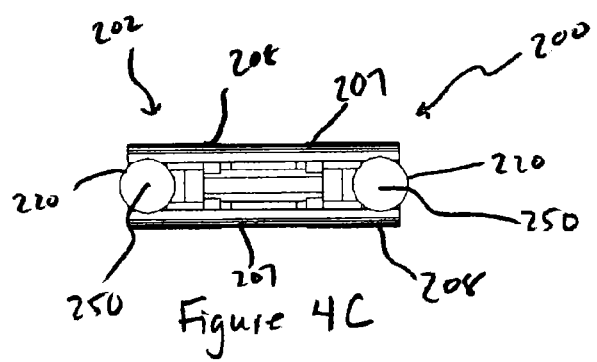
FIG. 4C is an end view of the distractible intervertebral body fusion device of FIG. 4A.

Referring now to FIGS. 4A-4C, there can be seen another embodiment of a distractible intervertebral fusion device 200 according to an aspect of the present invention. This embodiment of the device 200 similarly includes a device body 202 having a pair of opposed base plates 208 with outer bearing surfaces 207 connected with arms 210 that are distractible with threaded members 220. In this embodiment, threaded members 220 are positioned outside of arms 210, as opposed to device 100, where the threaded members 120 are positioned inside of the arms 110. This provides for additional space between insertion tools 250 and threaded members 220 for delivering bone growth stimulant to aid in vertebral fusion following distraction. Additionally the external location of the screws may enhance the ability of the device to carry torsional loading the device may experience during implantation or fusion.

Referring now to FIGS. 5A-5B and 6A-6B, there can be seen a further embodiment of a distractible intervertebral fusion device 300 according to an aspect of the present invention. Device 300 includes a device body 302 including a nose portion 304, a rear portion 306, a pair of opposed base plates 308 with outer bearing surfaces 307, and arms 310. Each arm 310 includes a pair of structural members 312 hingedly attached to each other and to one of the base plates 308. In one embodiment, structural members 312 are hinged to each other and to base plates 308 with pins 314. Device 300 can have arms 310 on both side 316, 318 of device 300.

Figure 7:
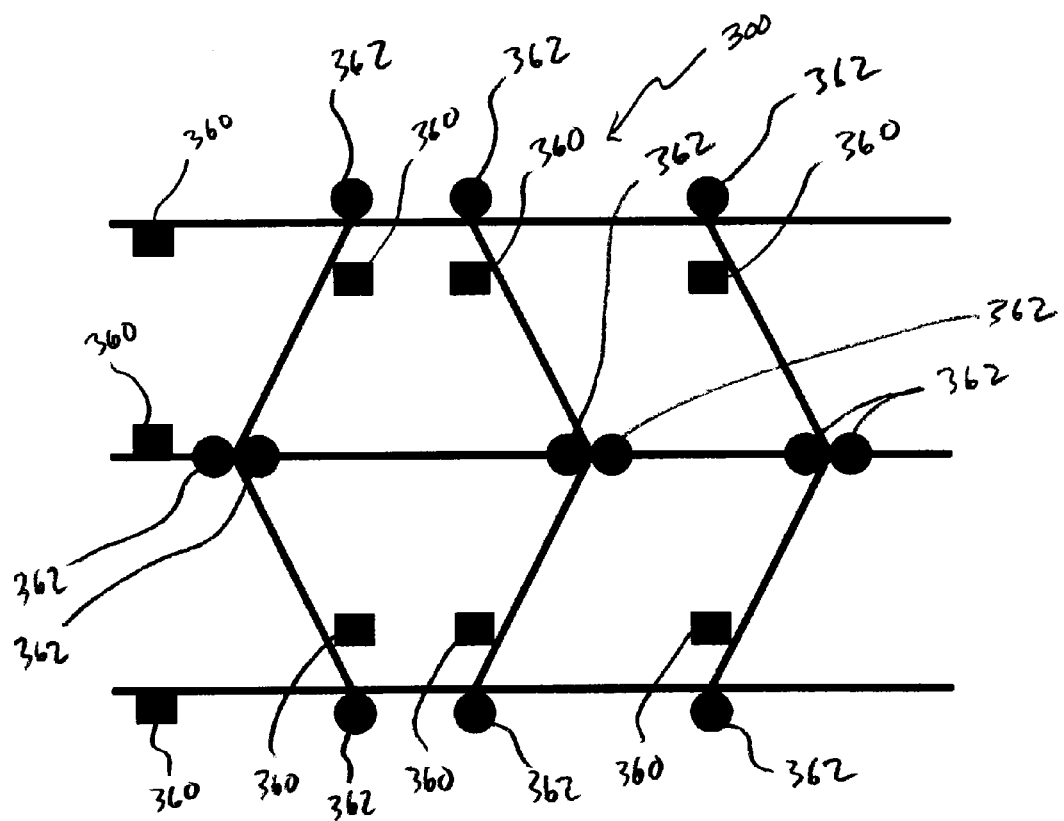
FIG. 7 is a simplified view of the distractible intervertebral body fusion device of FIG. 5A.
Figure 9A:
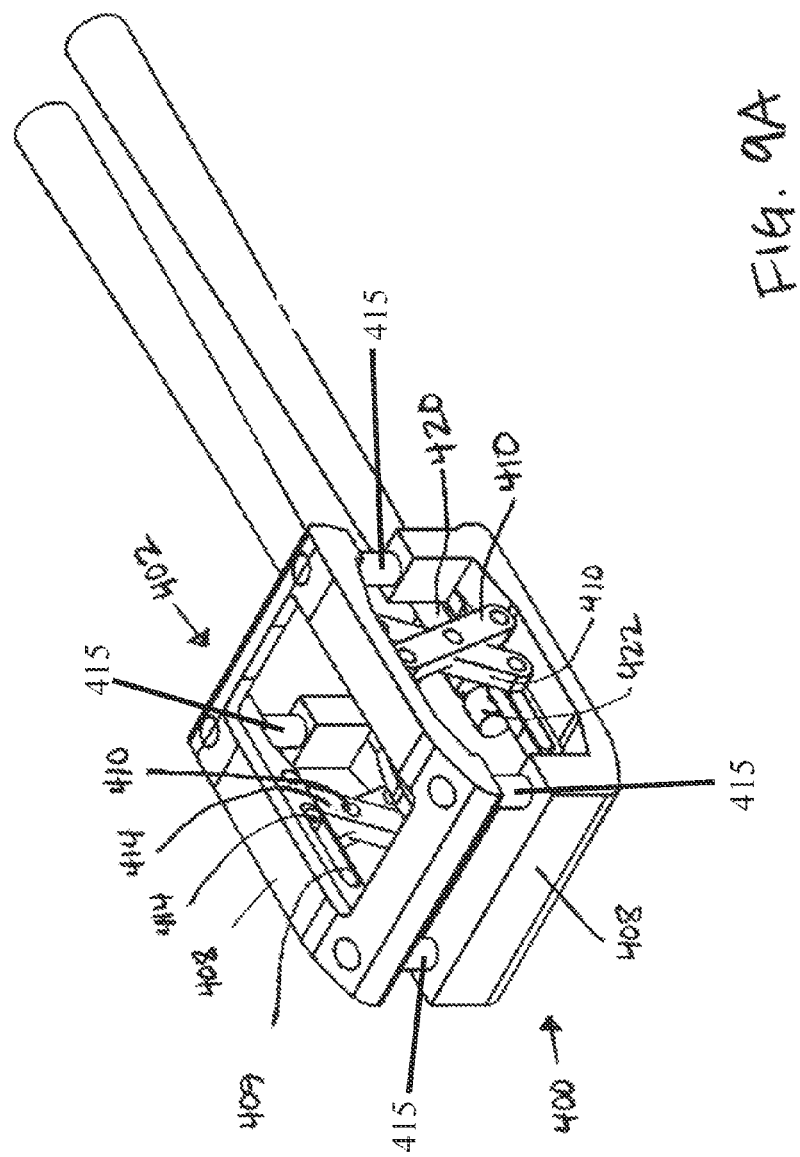
FIG. 9A is a perspective view of the distractible intervertebral body fusion device of FIG. 8A in an expanded configuration.
Figure 10A:
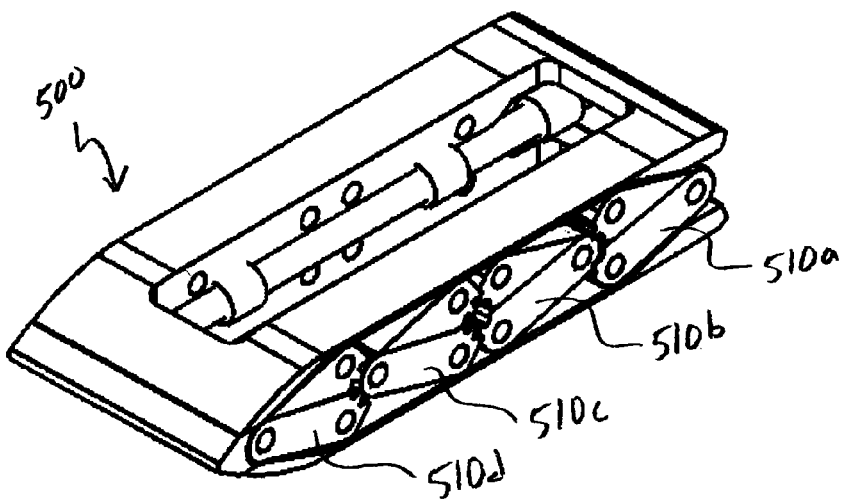
FIG. 10A is a perspective view of a distractible intervertebral body fusion device according to an aspect of the present invention.
Figure 10B:
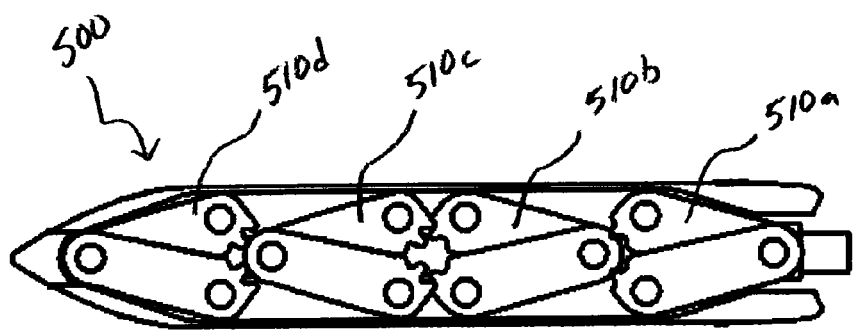
FIG. 10B is a side view of the distractible intervertebral body fusion device of FIG. 10A.
Figure 11A:
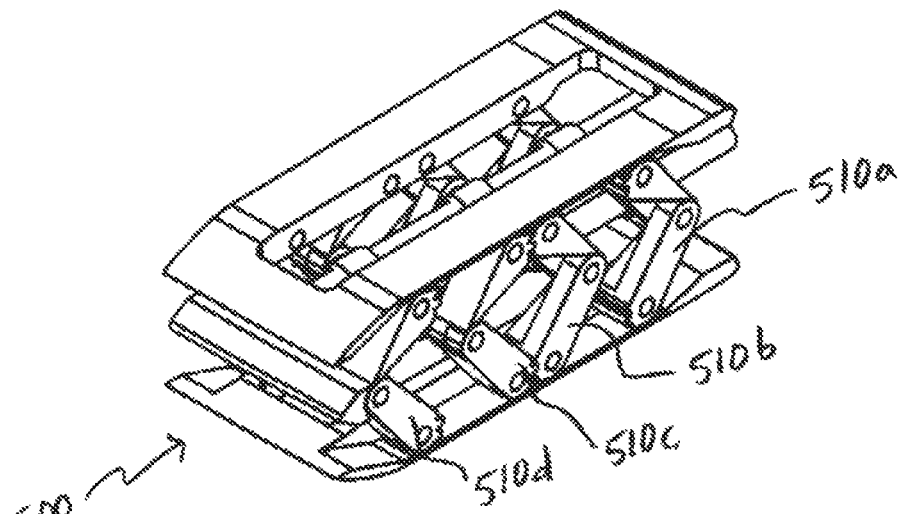
FIG. 11A is a perspective view of the distractible intervertebral body fusion device of FIG. 10A in an expanded configuration.
Figure 11B:
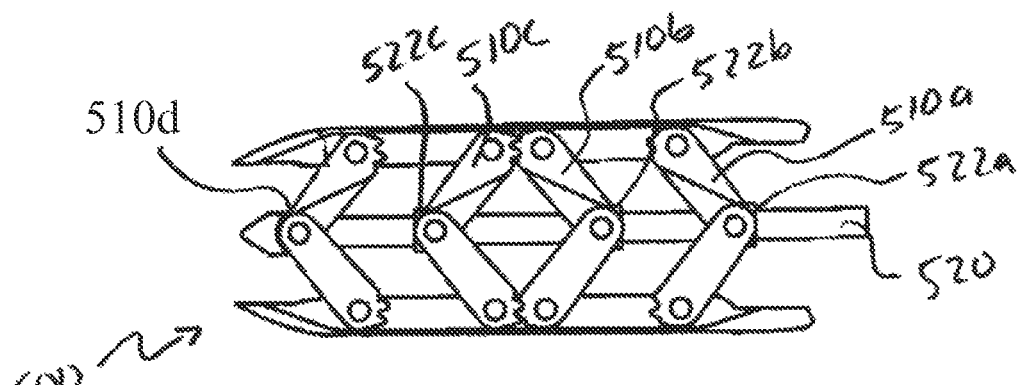
FIG. 11B is a side view of the distractible intervertebral body fusion device of FIG. 10A in an expanded configuration.
Figure 11C:
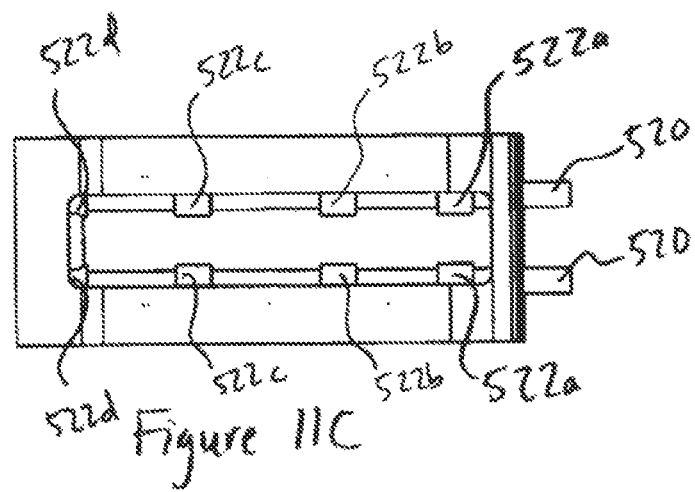
FIG. 11C is a top view of the distractible intervertebral body fusion device of FIG. 10A in an expanded configuration.

Device 300 can include a third arm 310c in addition to a first arm 310a and second arm 310b. In one embodiment, third arm 310c is attached to base plates 308 with the same pins 314 as second arm 310b. In another embodiment, third arm 310c is separately hinged to base plates 308. Third arm 310c can be positioned at any point along base plates 108 between nose portion 304 and rear portion 306. Third arm 310c provides a means for stably maintaining the device 300 under in-vivo loads when in a distracted position. As is demonstrated by a simplified form of device 300 shown in FIG. 7, device 300 can stably support the disc space because it has zero degrees of freedom once locked in the distracted position with threaded members 320 in place. From Gruebler's equation, the number of degrees of freedom=3*(n−1)−2f, where n is the number of links 360 in the linkage and f is the number of one degree of freedom kinematic pairs 362 in the linkage. As is shown in FIG. 7, the device 300 has 9 links and 12 kinematic pairs, so 3*(9−1)−2*12=0 degrees of freedom.

Optionally, and in the example of embodiment 300 where the rigid links 310c and 310b share a common hinge 314, the rigid link 310a may be slightly longer than either 310c or 310b thus resulting in the rear portion 306 of the device 300 having a distracted height that is slightly greater than the distracted height of the nose portion 304 of the device 300. Additionally block 322a may be supplemented with a differential screw mechanism that would allow the position of block 322a to be independently controlled with respect to block 322b. Such control of 322a would allow the lordosis, or angular orientation of the endplates, to be matched exactly to the unique lordosis, or desired lordosis, of a patient's spine. Specifically, the differential screw mechanism would be accomplished by threading an internally and externally threaded cylinder over the threaded member 320 but within the block 322a. The threaded cylinder could then be removeably coupled to an external drive device as threaded member 320 is removeably coupled to insertion tool 350.

Additionally, with embodiment 300, when portions of the threaded members are not reverse threaded and clearance exists in block 322c the device may be able to be gently and additionally distracted due to in-vivo axial tension as the clearance in block 322c allows block 322c to slide closer to block 322b and block 322a. However, having distracted slightly under tensile loading the device would return to the original height as compressive loading is returned. The parallelism would remain unchanged, while lordotic endplates may undergo a small angular displacement that would return to the set lordosis with the reapplication of the normal compressive loading. This extensibility of the device could offer great benefits to the fusion process as the endplates, which may be growing into the endplates of the vertebral bodies, would not be pulled away, damaging early bone growth, from the endplates by motion of the patient's spine.

Figure 5A:
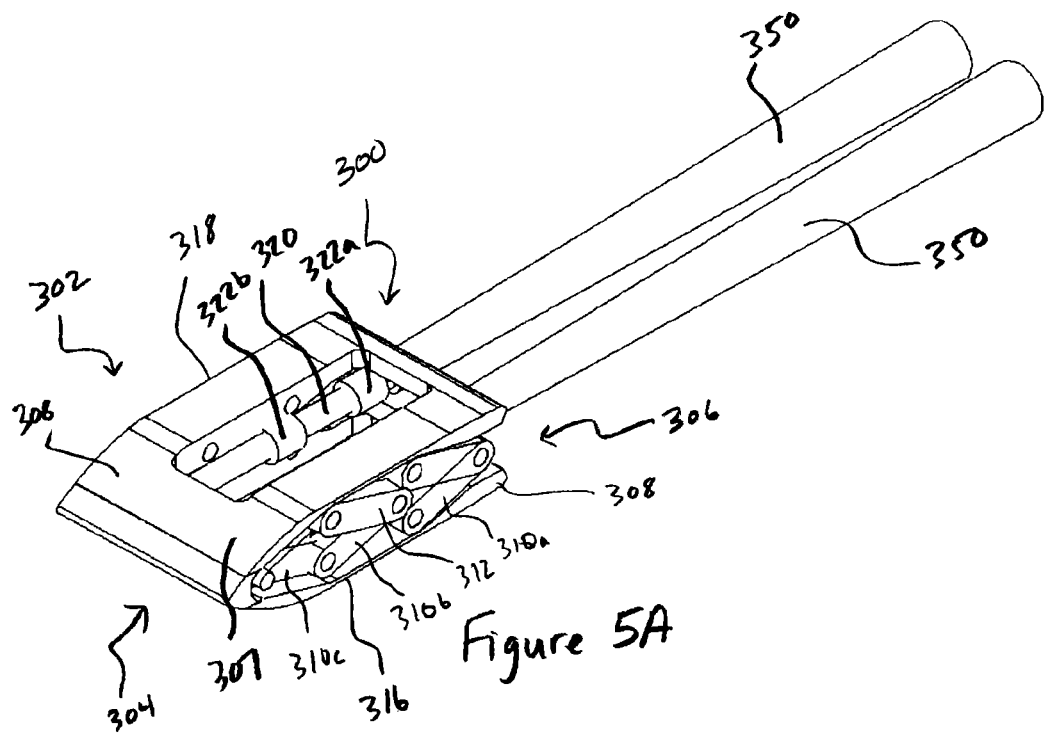
FIG. 5A is a perspective view of a distractible intervertebral body fusion device according to an aspect of the present invention.
Figure 5B:
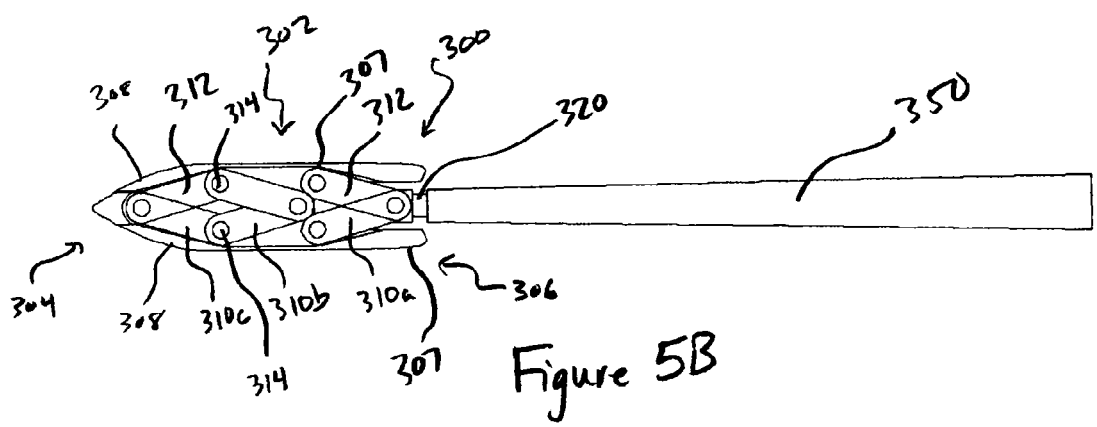
FIG. 5B is a side view of the distractible intervertebral body fusion device of FIG. 5A.
Figure 6A:
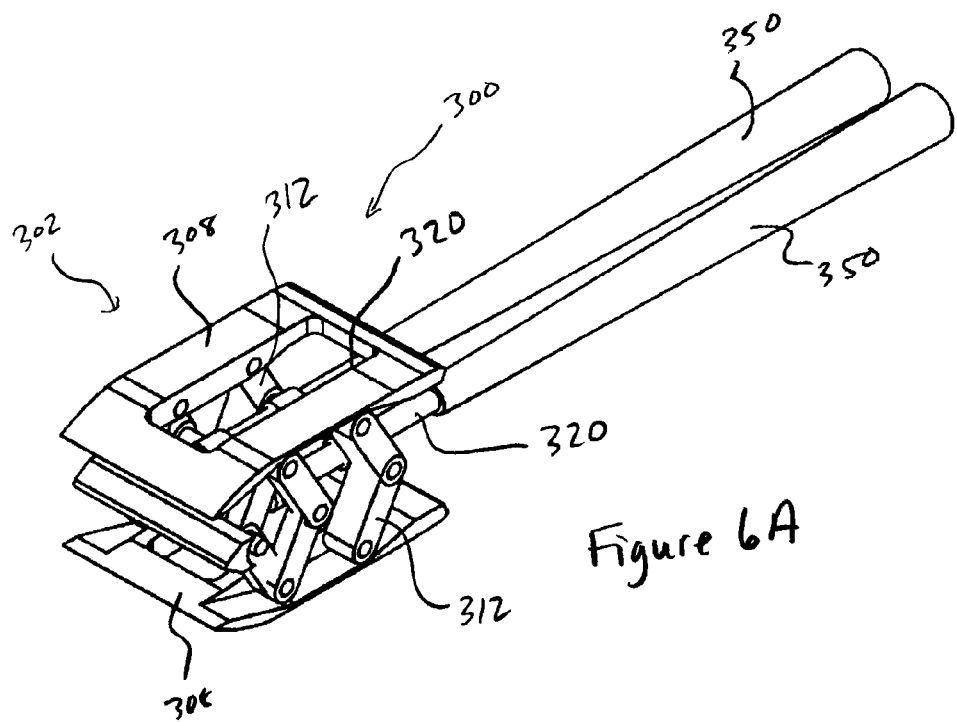
FIG. 6A is a perspective view of the distractible intervertebral body fusion device of FIG. 5A in an expanded configuration.
Figure 6B:
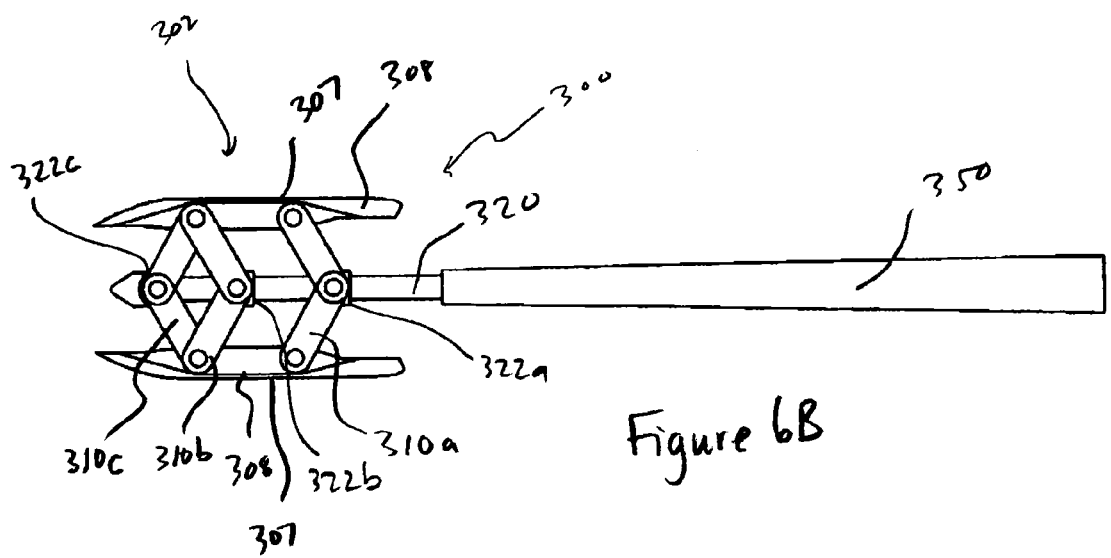
FIG. 6B is a side view of the distractible intervertebral body fusion device of FIG. 5A in an expanded configuration.

As with device 100 and device 200, threaded members 320, such as screws, and insertion tool 350 can be used to distract device from the compressed state shown in FIGS. 5A and 5B to a distracted state, such as the one shown in FIGS. 6A and 6B. Because device 300 has three arms 310, threaded members 320 are inserted through first blocks 322a attached to the first arms 310a, through second blocks 322b attached to the second arms 310b, and into third blocks 322c attached to the third arms 310c. Actuation of threaded members 320 in a first direction drives blocks 322 closer together, which causes expansion of arms 310 and distraction of base plates 308. Actuation of threaded members 320 in the opposite direction would drive blocks 322 apart, thereby bringing base plates 308 closer together. In one embodiment, blocks 322a and 322b can be tapped to accommodate threaded members 320 and blocks 322c can provide a clearance fit with threaded members 320. When threaded members 120 are actuated, this allows blocks 322c to be pulled towards blocks 322a, 322b, causing the device 300 to distract.

In another embodiment depicted in FIGS. 10A-10B and 11A-11C, a distractible intervertebral body fusion device 500 can include a fourth arm 510d in addition to first 510a, second 510b, and third 510c arms. Device 500 can also include a corresponding fourth block 522d connected to fourth arm 510d in addition to first 522a, second 522b, and third 522c arms through which threaded members 520 extend. The device 500 is also capable of stably supporting the disc space. In fact, the device 500 is actually over-constrained in that it has additional constraints (i.e., a fourth arm 510d) over and above what is necessary to constrain the device 500 to have zero degrees of freedom.

Referring now to FIGS. 8A-8B and 9A-9B there can be seen a further embodiment of a distractible intervertebral fusion device 400 according to an aspect of the present invention. Device 400 includes a device body 402 including a nose portion 404, a rear portion 406, a pair of opposed base plates 408 having outer bearing surfaces 407, and arms 410. Device 400 can have arms 410 on both side 416, 418 of device 400.

Arms 410 of device 400 are hingedly attached to each other with a pin 414. In one embodiment, arms 410 comprise a single structural member 412 and form a generally x-shape with each other. Each arm 410 has one end hingedly attached to one of the base plates 408 and the other end slidably attached to a slot 409 in the opposite base plate 408. As with the previously described devices, the device 400 is distracted from the compressed configuration shown in FIGS. 8A and 8B to an expanded configuration such as the one shown in FIGS. 9A and 9B by rotating a threaded member 420 within blocks 422 attached to arms 410. In this embodiment, as the blocks 422 are drawn closer together, the pins 414 slidably disposed within slots 409 translate within slots 409 from an end nearest the nose portion 404 towards an end nearest the rear portion 406 to allow arms 410 to expand, which causes base plates 408 to distract. This device also stably supports the disc space. The device has four rigid links, two one-degree of freedom kinematic pairs (pinned joints), and two two-degree of freedom kinematic pairs (slidably disposed joints) that may be locked in place within the slots 409 making them one degree of freedom kinematic pairs. Prior to locking the pins within slots, the device would have $3(4-1)-2(3)-1(2)=1$ degree of freedom and post locking the device would have $3(4-1)-2(5)=-1$ degree of freedom. Additionally, the slidably disposed joints could be considered to be axially locked at all times while mounted on the threaded members 420 thus having $3(4-1)-2(5)=-1$ degree of freedom and exhibiting stability.

Optionally, the device 400 could be constructed such that both ends of each arm 410 and the pins 414 to which the arms 410 are affixed are slidably disposed within a broader slot 409 and the arm assembly remains centered along the length of the device by translationally fixing the threaded member 420 along its length while allowing it to rotate. As in previous optional embodiments, portions of the threaded member 420 could be reverse threaded such that turning the threaded member 420 would move threaded block 422 and its reverse threaded complement towards each other. Additionally a hybrid of this embodiment 400 and the embodiment 100 presented in FIG. 1A could be created such that the slidably disposed mechanism of embodiment 400 could be implemented as the drive mechanism on the bottom plate 408 and the pinned hinges 114 with gear teeth 111 can be used as the means of stabilizing the top plate 108. In this hybrid design the links may not be crossed as in the embodiment 400. Instead, the links could be configured similarly to a horizontally mirrored pair of links 112 of embodiment 100.

Referring again to FIGS. 8A-8B and 9A-9B, in certain embodiments, devices can also include pins 415 extending vertically through devices and slidably disposed within or relative to one of the endplates, either top or bottom, of the device. Pins 415 add torsional stiffness to the device to help keep the end plates parallel during distraction. Pins can be of any shape, such as for, example, rectangular, circular, elliptical, oblong, or hexagonal. In-vivo torsion may be one of the major challenges prohibiting the successful approval and market release of low-profile distractable fusion-devices. In-vivo dynamic torsional loading may exceed 10 [Nm] and static torsional loading may exceed 10-20 [Nm]. A device having titanium (or exhibiting the mechanical properties of common medical grade alloys of titanium) pins mounted vertically at the four corners of the device, when viewed from the top, each approximately 15 [mm] from the vertical axis of torsion of the device would require pin diameters of 2-3 [mm] to prevent the device from deflecting more than 1 [deg] due to said torsional loading. Without pins, sustaining nearly 5 million cycles of 10 [Nm] torsional loading could cause serious failure to any device with intricate welds and the inevitable stress risers inherent to the small radii and tight curvatures inherent to complex micro-machined components. The pins also help to support the in-vivo dynamic shear load which can be greater than 600 to 750 [N] with an additional and often equal, in magnitude, compressive component. Although depicted as having four pins at the corners of the device, it should be understood that different numbers of pins in various locations can be utilized.

Although the various devices described herein are described as being brought from a compressed configuration to an expanded configuration by rotation of a threaded member, the devices can be distracted by any other type of actuation member. In some embodiments, mechanisms other than threaded members can be used to distract the device. Such mechanisms include, for example, a pop-rivet mechanism, a sardine key and ribbon, a tourniquet and wire, a saw blade/ratchet, a zip-tie-like mechanism, piezo-electric inch worm motors and shape changing materials such as a shape member alloy or a conducting polymer actuator. These alternative locking mechanisms could be designed to make the device behave as if it were locked with a threaded member, preventing the device from being compressed as well as extended, or these mechanisms could afford the device the capability to ratchet upwards post implantation if such action would benefit the patient or provide additional therapy.

Various embodiments of implantation procedures for the disclosed embodiments of distractible intervertebral fusion devices may be as follows:

Lumbar: A lumbar implant can be 6 mm in height, expandable to 12 mm in height, with a length of 25-30 mm and a width of 6 mm. The implant can be inserted through a minimally invasive tubular port that goes through the muscle of the lumbar spine and into the lumbar disc space. Prior to inserting the implant, the lumbar disc should be completely removed.

Cervical: A cervical implant can be 6 mm in height, expandable to 10 mm in height, with a length of 10 mm and a width of 6 mm. The implant can be inserted after anterior cervical surgical exposure. The cervical disc should be completely removed prior to insertion of the implant.

Various embodiments of systems, devices and methods have been described herein. These embodiments are given only by way of example and are not intended to limit the scope of the present invention. It should be appreciated, moreover, that the various features of the embodiments that have been described may be combined in various ways to produce numerous additional embodiments. Moreover, while various materials, dimensions, shapes, implantation locations, etc. have been described for use with disclosed embodiments, others besides those disclosed may be utilized without exceeding the scope of the invention.

The invention claimed is:

1. A distractible intervertebral body fusion device for implantation into an intervertebral disc space in a patient's body, comprising:
   a top base plate having a top bearing surface configured to interface with an end plate of a superior vertebra of the intervertebral disc space;
   a bottom base plate having a bottom bearing surface configured to interface with an end plate of an inferior vertebra of the intervertebral disc space;
   a first arm hingedly connected to the top base plate and the bottom base plate;
   a second arm hingedly connected to the top base plate and the bottom base plate;
   an actuation member extending through the first arm and into the second arm, the actuation member configured such that actuation of the actuation member causes expansion of the first arm and second arm such that the top bearing surface and bottom bearing surface move away from each other into a distracted position, wherein the actuation member is threaded and is actuated by rotating the actuation member and the first arm includes a threaded portion through which the actuation member is inserted and the actuation member is attached to the second arm such that rotation of the actuation member in a first direction pulls the second arm towards the first arm without the actuation member moving translationally through the device and rotation of the actuation member in a second direction pushes the second arm away from the first arm without the actuation member moving translationally through the device;
   a third arm disposed adjacent the first arm and hingedly connected to the top base plate and the bottom base plate;
   a fourth arm disposed adjacent the second arm and hingedly connected to the top base plate and the bottom base plate;
   a second actuation member extending through the third arm and into the fourth arm, the second actuation member configured such that actuation of the actuation member in a first direction causes expansion of the third arm and the fourth arm, wherein the second actuation member is threaded and is actuated by rotating the second actuation member and the third arm includes a threaded portion through which the second actuation member is inserted and the actuation member is attached to the fourth arm such that rotation of the second actuation member in a first direction pulls the fourth arm towards the third arm without the second actuation member moving translationally through the device and rotation of the second actuation member in a second direction pushes the fourth arm away from the third arm without the second actuation member moving translationally through the device,
   wherein the actuation member includes a first threaded portion that extends through the first arm and a second threaded portion that extends into the second arm and the second actuation member includes a first threaded portion that extends through the third arm and a second threaded portion that extends into the fourth arm, and wherein the first threaded portion and the second threaded portion of each of the actuation members are reverse threaded relative to each other to cause the actuation members to remain translationally stationary when rotated in both the first direction and second direction; and
   means for stabilizing the top base plate and bottom base plate such that the device has zero, or fewer, degrees of freedom of movement in the distracted position, and wherein the device is designed to remain in the body and stably maintain the intervertebral disc space during vertebral fusion while in the distracted position.

2. The device of claim 1, wherein each arm comprises two hingedly connected structural members.

3. The device of claim 1, wherein the actuation member and the second actuation member are configured to be actuated in unison with one another.

4. The device of claim 1, wherein the actuation member and the second actuation member are capable of being actuated independently of each other.

5. The device of claim 1, wherein the top base plate and bottom base plate each have an opening defined therein configured to allow bone growth into an open space defined by the device.

6. The device of claim 1, further comprising one or more pins extending between said top base plate and said bottom base plate and slidably disposed relative to one of the base plates.

7. The device of claim 6, wherein there are four pins, each pin disposed proximate a corner of the device.

8. The device of claim 1, wherein the actuation member is connected to the second arm via a clearance fit and the second actuation member is connected to the fourth arm via a clearance fit.

9. A distractible intervertebral body fusion device for implantation into an intervertebral disc space in a patient's body, comprising:
   a top base plate having a top bearing surface configured to interface with an end plate of a superior vertebra of the intervertebral disc space;
   a bottom base plate having a bottom bearing surface configured to interface with an end plate of an inferior vertebra of the intervertebral disc space;
   a first arm and an opposing second arm, each arm including a pair of structural members hingedly attached to each other, with each structural member hingedly attached to one of the top base and the bottom base, wherein each structural member of the first arm interlocks with one of the structural members of the second arm via complementary gear teeth;
   a third arm and an opposing fourth arm on an opposite side of the device from the first arm and the second arm, each arm including a pair of structural members hingedly attached to each other, with each structural member hingedly attached to one of the top base and the bottom base, wherein each structural member of the third arm interlocks with one of the structural members of the fourth arm via complementary gear teeth;

a first threaded actuation member extending through a threaded portion of the first arm and attached to the second arm, the first actuation member configured such that rotation of the first actuation member in a first direction causes expansion of the first arm and second arm by pulling the second arm towards the first arm causing the top bearing surface and bottom bearing surface to move away from each other into a distracted position and rotation of the first actuation member in a second direction pushes the second arm away from the first arm causing the top bearing surface and bottom bearing surface to move towards each other, the first actuation member remaining translationally stationary with respect to the device when rotated in both the first direction and the second direction; and a second threaded actuation member extending through a threaded portion of the third arm and attached to the fourth arm, the second actuation member configured such that rotation of the second actuation member in a first direction causes expansion of the third arm and fourth arm by pulling the fourth arm towards the third arm causing the top bearing surface and bottom bearing surface to move away from each other into a distracted position and rotation of the second actuation member in a second direction pushes the fourth arm away from the third arm causing the top bearing surface and bottom bearing surface to move towards each other, the first actuation member remaining translationally stationary with respect to the device when rotated in both the first direction and the second direction, wherein the first actuation member includes a first threaded portion that extends through the first arm and a second threaded portion that extends into the second arm and the second actuation member includes a first threaded portion that extends through the third arm and a second threaded portion that extends into the fourth arm, and wherein the first threaded portion and the second threaded portion of each of the actuation members are reverse threaded relative to each other to cause the actuation members to remain translationally stationary when rotated in both the first direction and second direction.

10. The device of claim 9, wherein the first actuation member and the second actuation member are configured to be actuated in unison with one another.

11. The device of claim 9, wherein the first actuation member and the second actuation member are capable of being actuated independently of each other.

12. The device of claim 9, wherein the top base plate and bottom base plate each have an opening defined therein configured to allow bone growth into an open space defined by the device.

13. The device of claim 9, wherein the first actuation member is connected to the second arm via a clearance fit and the second actuation member is connected to the fourth arm via a clearance fit.

* * * * *

UNITED STATES PATENT AND TRADEMARK OFFICE
CERTIFICATE OF CORRECTION

PATENT NO. : 8,628,577 B1  
APPLICATION NO. : 12/407608  
DATED : January 14, 2014  
INVENTOR(S) : Omar F. Jimenez It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 440 days.

Signed and Sealed this
Eleventh Day of August, 2015

Michelle K. Lee
*Director of the United States Patent and Trademark Office*